(12) United States Patent
Dumoulin

(10) Patent No.: US 10,980,442 B2
(45) Date of Patent: *Apr. 20, 2021

(54) MRI TRANSFER TABLE ASSEMBLY AND CART APPARATUS

(71) Applicant: Children's Hospital Medical Center, Cincinnati, OH (US)

(72) Inventor: Charles L. Dumoulin, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 443 days.

This patent is subject to a terminal disclaimer.

(21) Appl. No.: 15/968,168

(22) Filed: May 1, 2018

(65) Prior Publication Data
US 2018/0242879 A1 Aug. 30, 2018

Related U.S. Application Data

(63) Continuation of application No. 14/376,523, filed as application No. PCT/US2012/052249 on Aug. 24, 2012, now Pat. No. 9,968,279.

(60) Provisional application No. 61/593,930, filed on Feb. 2, 2012.

(51) Int. Cl.
*A61B 5/00* (2006.01)
*A61B 5/055* (2006.01)
*A61G 11/00* (2006.01)
*G01G 19/44* (2006.01)

(52) U.S. Cl.
CPC .......... *A61B 5/0555* (2013.01); *A61B 5/0046* (2013.01); *A61G 11/005* (2013.01); *G01G 19/44* (2013.01); *A61B 2503/045* (2013.01)

(58) Field of Classification Search
CPC ................ A61B 5/0555; A61B 5/0046; A61B 2503/045; A61G 11/005; G01G 19/44
See application file for complete search history.

(56) References Cited

U.S. PATENT DOCUMENTS

| | | |
|---|---|---|
| 4,665,364 A | 5/1987 | Hanawa |
| 4,727,328 A | 2/1988 | Carper et al. |
| 5,178,146 A | 1/1993 | Giese |

(Continued)

FOREIGN PATENT DOCUMENTS

| | | |
|---|---|---|
| WO | WO 1996/029932 A1 | 10/1996 |
| WO | WO 2013/001847 A1 | 1/2013 |

(Continued)

OTHER PUBLICATIONS

Extended European Search report from EP application 12867342, dated Jul. 1, 2015, 7 pages, mailed from European Patent Office, Munich, Germany.

(Continued)

*Primary Examiner* — Joel Lamprecht
(74) *Attorney, Agent, or Firm* — BakerHostetler

(57) ABSTRACT

The present disclosure relates to a transfer table assembly and cart apparatus suitable for use in association with an MR scanner. The transfer table assembly may include a transfer table base and a supporting mechanism coupling the transfer table base to a transfer table cart in a cantilevered fashion at substantially the same level of a scanning bore of an MR scanner. The transfer table cart may include a frame designed to dock with the MR scanner.

28 Claims, 8 Drawing Sheets

(56) References Cited

U.S. PATENT DOCUMENTS

| | | |
|---|---|---|
| 5,515,415 A | 5/1996 | Herrmann et al. |
| 5,619,763 A | 4/1997 | Randolph et al. |
| 5,650,724 A | 7/1997 | Yamagata |
| 5,724,970 A | 3/1998 | Votruba et al. |
| 5,792,041 A | 8/1998 | Kobayashi et al. |
| 5,800,335 A | 9/1998 | Koch et al. |
| 6,101,644 A | 8/2000 | Gagneur et al. |
| 6,377,047 B1 | 4/2002 | Wong et al. |
| 6,611,702 B2 | 8/2003 | Rohling et al. |
| 6,718,571 B2 | 4/2004 | Bartels |
| 6,854,140 B2 | 2/2005 | Bartels et al. |
| 7,093,311 B2 | 8/2006 | Gnoyke |
| 7,131,769 B2 | 11/2006 | Vezina |
| 7,216,383 B2 | 5/2007 | Heinl et al. |
| 7,467,004 B2 | 12/2008 | Calderon et al. |
| 7,599,728 B2 | 10/2009 | Feenan |
| 7,634,827 B2 | 12/2009 | Gagneur et al. |
| 7,827,635 B2 | 11/2010 | Wang et al. |
| 7,850,595 B2 | 12/2010 | White |
| 7,869,858 B2 | 1/2011 | Calderon et al. |
| 7,874,030 B2 | 1/2011 | Cho et al. |
| 7,920,910 B2 | 4/2011 | Calderon et al. |
| 8,147,396 B2 | 4/2012 | Srinivasan |
| 8,276,225 B2 | 10/2012 | Kogan et al. |
| 9,968,279 B2 * | 5/2018 | Dumoulin .............. G01G 19/44 |
| 2001/0052168 A1 | 12/2001 | Haase et al. |
| 2002/0104163 A1 | 8/2002 | Reimann |
| 2002/0158720 A1 | 10/2002 | Weyers et al. |
| 2002/0173717 A1 | 11/2002 | Rohling et al. |
| 2003/0153805 A1 | 8/2003 | Gryn et al. |
| 2005/0034237 A1 | 2/2005 | Lenting et al. |
| 2005/0113668 A1 | 5/2005 | Srinivasan |
| 2006/0293589 A1 | 12/2006 | Calderon et al. |
| 2007/0132581 A1 | 6/2007 | Molyneaux et al. |
| 2007/0232894 A1 | 10/2007 | Feenan |
| 2008/0117044 A1 | 5/2008 | Hibbs |
| 2008/0201849 A1 | 8/2008 | Van Es et al. |
| 2009/0000917 A1 | 1/2009 | Tigwell et al. |
| 2009/0027053 A1 | 1/2009 | Decke et al. |
| 2009/0083907 A1 | 4/2009 | Ahlman |
| 2010/0185045 A1 | 7/2010 | Chinn |
| 2011/0113555 A1 | 5/2011 | Smith |
| 2011/0145991 A1 | 6/2011 | Bridge et al. |
| 2012/0071745 A1 | 3/2012 | Rapoport |
| 2013/0025054 A1 | 1/2013 | Graw et al. |
| 2013/0109956 A1 | 5/2013 | Rapoport |
| 2013/0150656 A1 | 6/2013 | Falk et al. |

FOREIGN PATENT DOCUMENTS

| | | |
|---|---|---|
| WO | WO 2013/115846 A1 | 8/2013 |
| WO | WO 2013/115847 A1 | 8/2013 |
| WO | WO 2013/115848 A1 | 8/2013 |

OTHER PUBLICATIONS

Dumoulin, Charles L., et al., Magnetic Resonance Imaging Compatible Neonate Incubator, Magnetic Resonance Engineering, Jun. 28, 2002, vol. 15 (2), pp. 117-128.

European Patent Application No. 12867132.8; Extended Search Report; dated Sep. 16, 2015; 6 pages.

European Patent Application No. 12867263.1; Extended Search Report; dated Sep. 16, 2015; 7 pages.

Dumoulin, Charles L., et al., Magnetic Resonance Imaging Compatible Neonate Incubator, Magnetic Resonance Engineering, Jun. 28, 2002, vol. 15 (2), pp. 117-128, US.

PCT International Search Report/Written Opinion, PCT/US2012/052242, dated Nov. 2, 2012.

PCT International Search Report/Written Opinion, PCT/US2012/052249, dated Nov. 2, 2012.

PCT International Search Report/Written Opinion, PCT/US2012/052260 dated Nov. 2, 2012.

Ireland et al.; "A Novel Acoustically Quiet Coil for Neonatal MRI System"; Magnetic Resonance Engineering; vol. 45 No. 3; Aug. 2015; 8 pages.

European Patent Application No. 18202505.6; Extended Search Report; dated Jun. 5, 2019; 6 pages.

* cited by examiner

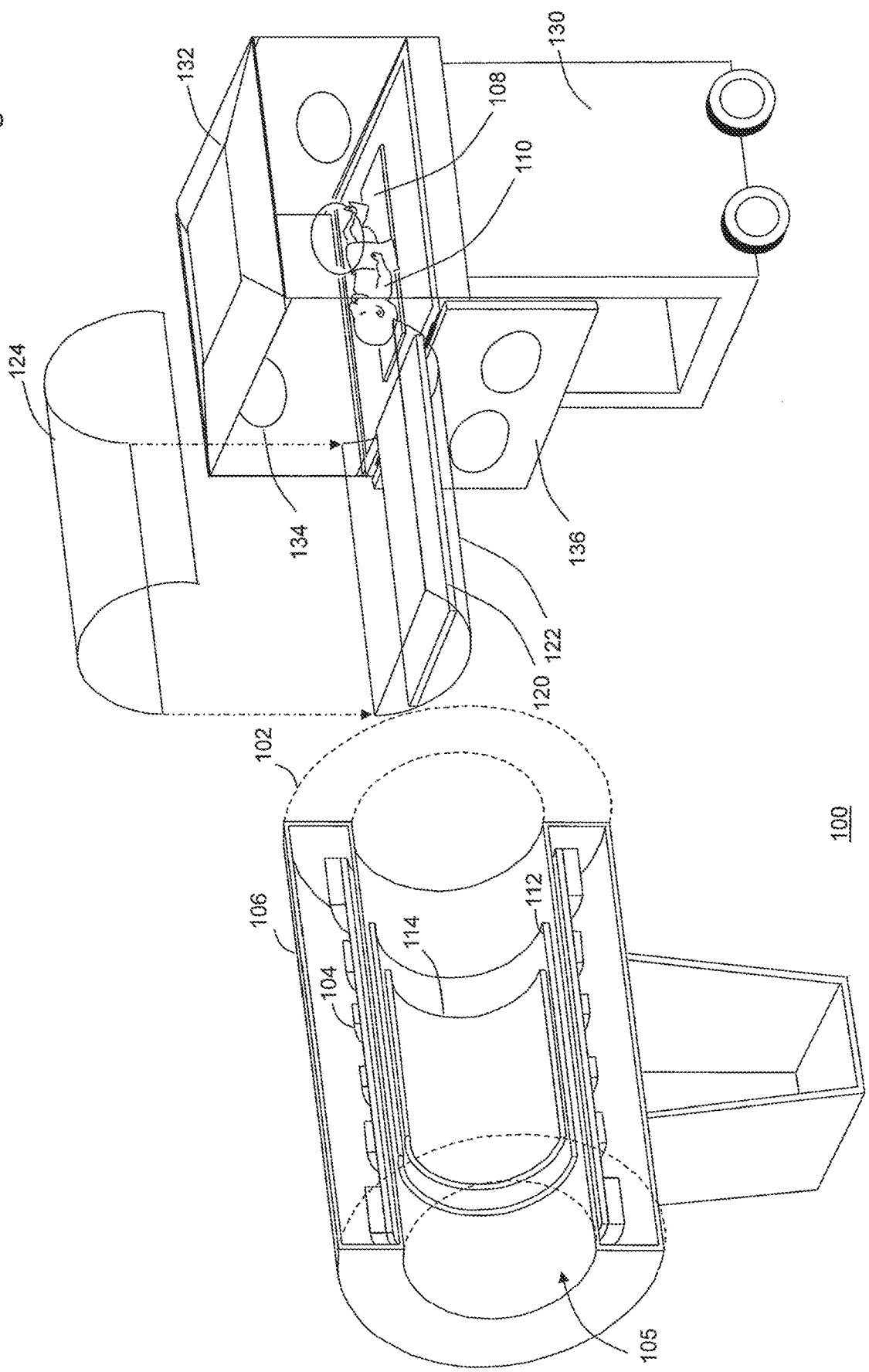

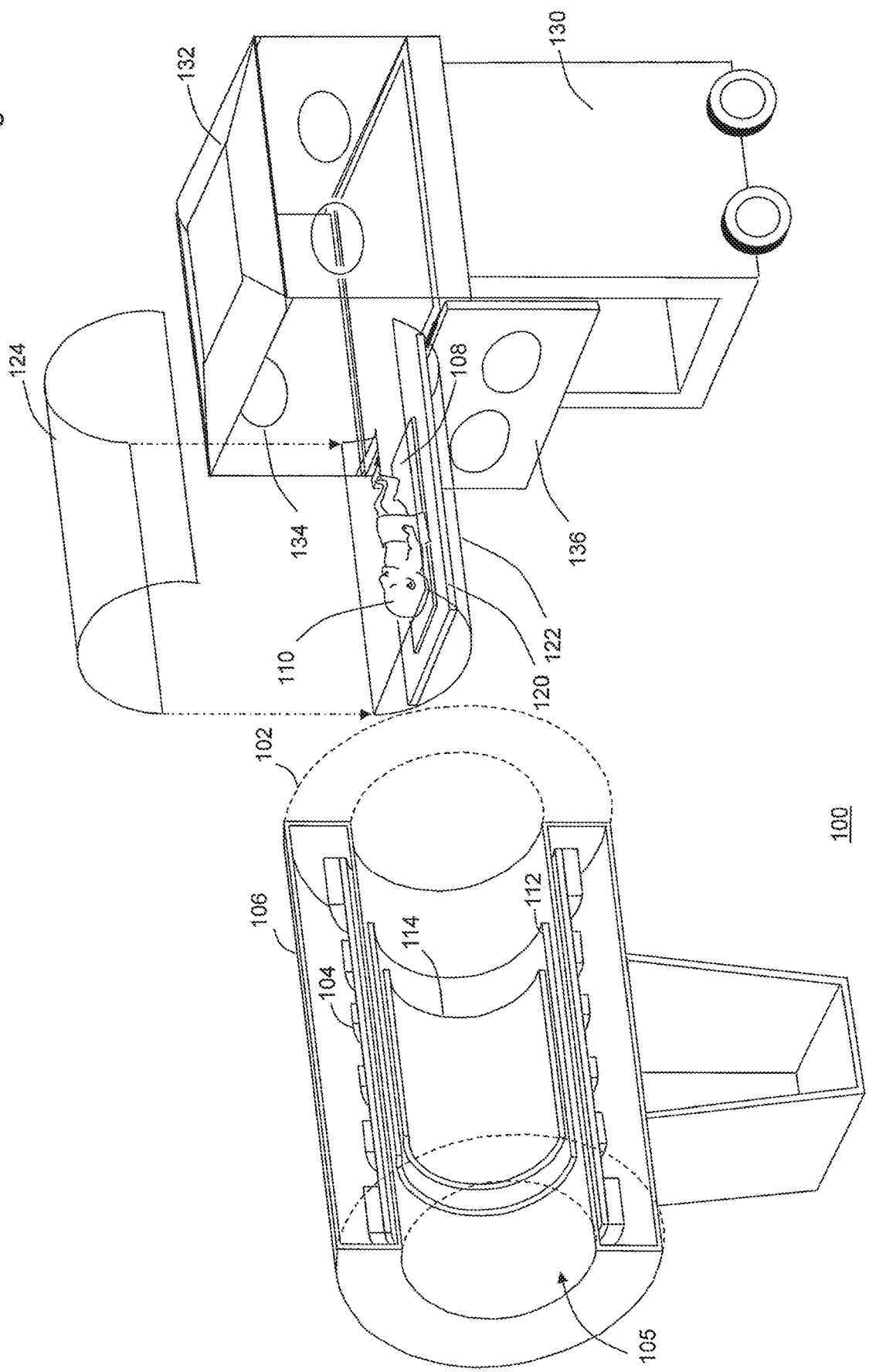

MRI TRANSFER TABLE ASSEMBLY AND CART APPARATUS

CROSS-REFERENCE TO RELATED APPLICATIONS

The present application is a continuation application of U.S. patent application Ser. No. 14/376,523 filed on Aug. 15, 2014 and scheduled to issue as U.S. Pat. No. 9,968,279 on May 15, 2018; which was a national stage entry of PCT/US2012/052249, filed Aug. 24, 2012; which claimed the benefit of U.S. Provisional Patent Application No. 61/593,930, filed Feb. 2, 2012. Each of the foregoing applications are hereby incorporated by reference.

FIELD OF THE DISCLOSURE

The present disclosure relates generally to magnetic resonance imaging equipment suitable for use in neonatal care and, more particularly, to a transfer table assembly for transferring a neonate from an incubator into an MR scanner.

BACKGROUND OF THE DISCLOSURE

Today premature infants weighing less than 1 kg may be stabilized and allowed to develop in neonatal intensive care units (NICUs). Magnetic resonance imaging (MM) is a powerful technique for diagnostic purposes but is not routinely performed on these infants due to a number of technical and logistical challenges.

When a mother has a high-risk pregnancy, it is possible that the baby could be born prematurely and would require treatment in a neonatal intensive care unit or NICU. Also, unexpected early delivery may require that an infant be treated in an NICU.

One difficulty in utilizing MRI for these premature infants is monitoring the vital signs and life support of the infant during MR examination. Parameters that must be monitored during examination include electrolyte levels, hydration and temperature. A second difficulty in utilizing MM is that the infant must be moved from an incubator or isolette into and out of the MR scanner. This movement places the infant at risk for injury.

Despite challenges, MM has the potential to play an important diagnostic role in the care and management of neonates. The full use of this imaging technique requires that the imaging take place as early as the first few hours of life. At this stage, however, the infants are hemodynamically unstable. Accordingly, transporting and maintaining homeostasis in these fragile infants presents difficulty.

Another challenge in using MRI for neonates is that MRI systems are frequently located in Radiology departments outside of and perhaps distant from the NICU. Consequently, the neonate must be escorted out of the NICU. This may present certain logistical and technical challenges with respect to controlling the neonate's environment. Furthermore, removing staff from the NICU to transfer and attend to one baby outside the NICU can place the remaining babies in the NICU at increased risk of a reduced level of care due to decreased staff coverage.

An MR compatible transport incubator and imaging system has been developed (Dumoulin et. al.) and is currently in use. Concepts in Magnetic Resonance (Magnetic Resonance Engineering), Vol. 15(2) 117-128 (2002). This system is a self-contained MR compatible transport incubator which carries the infant from the NICU to an MR scanner located in or near the NICU. With this approach the baby must first be transferred from its "home" incubator or isolette in the NICU into the transport incubator. The transport incubator is then moved to the MR scanner where it is docked with the scanner. A portion of the transport incubator containing the baby is then moved into the center of the MR imaging system magnet where MR imaging is performed. While this approach has the advantage of not disturbing the baby while it is in the transport incubator, even during MR scanning, it has several limitations including: a) infants must be fully detached from the monitoring equipment in their home incubator to be transferred into the transport incubator, b) the MR system that is used for imaging must have a bore large enough to accommodate the portion of the transport incubator containing the baby (thereby requiring a large heavy magnet), c) the baby and its attending staff need to leave the NICU for scanning, and d) because the transport incubator must be fully MR compatible while providing full life support for the baby, the system is heavy and expensive.

An alternate approach to provide MR imaging to newborn babies has been disclosed by Feenan in U.S. Pat. No. 7,599,728. In this approach a relatively smaller MR magnet is employed and MR-compatible incubators are docked to the magnet thereby permitting the baby to be slid into the magnet for imaging. While this approach has the benefit of providing a magnet that is more easily installed in the NICU, it does have several limitations including the need for MR compatible incubators to be used throughout the NICU, or the transfer of a neonate from a non-MR-compatible home incubator to an MR-compatible incubator. This approach also limits the access to the attending staff as they prepare the infant for MR scanning. In particular, the staff must reach through the incubator to push the baby into and out of the magnet.

In view of the foregoing, it may be understood that improved techniques for neonatal care necessitate improved transfer techniques for neonates in NICUs. In particular there is a need for an MR neonatal imaging system that can be easily sited in the NICU. The NICU magnet should be small, lightweight and acoustically quiet to permit installation within the physical boundaries of the NICU. Furthermore, there is a need for MR imaging of neonates without requiring them to be transferred out of their home incubators, or detaching them from their physiological monitoring systems or intravenous tubes. There is also a need to minimize physical movement of the baby as it enters the MR magnet and to ensure that it stays still during MR scanning. There is an additional need to for a neonatal MR imaging system that will allow babies in the NICU to be imaged without requiring that incubators in the NICU be MR compatible.

SUMMARY

A transfer table assembly is disclosed that is suitable for use in association with an MR scanner and an incubator for neonatal infants. The transfer table assembly generally includes a transfer table base that supports a transfer table. The transfer table may be removably connected with the top surface of the transfer table base. An associated incubator may include a bed for supporting a neonate when being cared for in the incubator. The transfer table may be configured to receive the incubator bed and the patient. In order to provide additional support and stability, the transfer table assembly may include an attachment mechanism for releasably attaching the transfer table base to the incubator in such a manner that said transfer table is substantially at the same level of the incubator bed. Additionally, the transport table assembly may include a supporting mechanism for providing additional structural support to the transfer table base when the transfer table base is attached to the incubator.

The present disclosure will now be described in more detail with reference to exemplary embodiments thereof as shown in the accompanying drawings. While the present disclosure is described below with reference to exemplary embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

FIG. 1b is a perspective view further showing the attachment of the transfer table assembly to an incubator in accordance with the present disclosure;

FIG. 1c is a perspective view showing the placement of a neonate into the transfer table assembly while attached to the incubator;

DETAILED DESCRIPTION

Figure 1A:
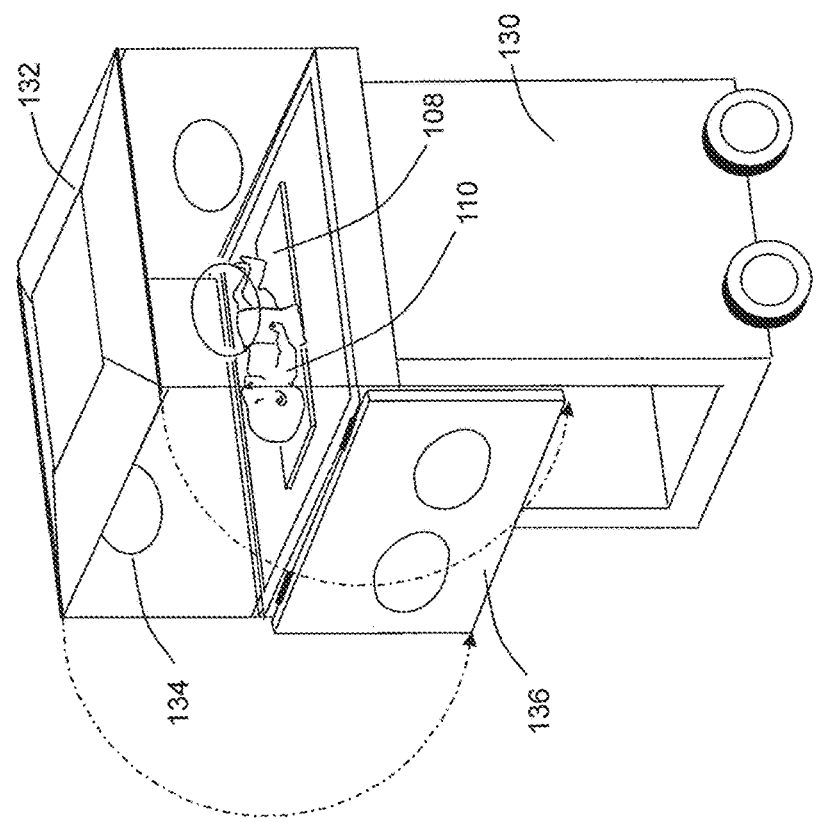
FIG. 1a is a perspective view of an exemplary MR imaging system and an exemplary incubator containing a neonate for use with the present disclosure.
Figure 1A:
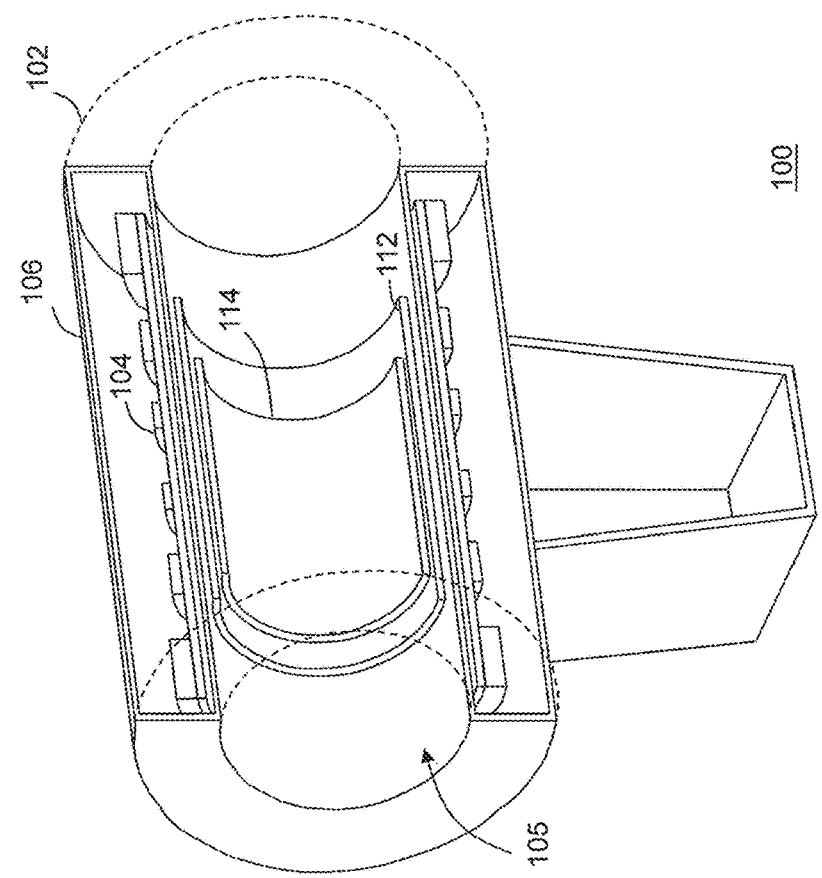

The use of MRI techniques for infants, and in particular neonates, is highly desirable. MRI techniques provide diagnostic information without patient exposure to ionizing radiation, and are suitable for extended and repeated studies.

MR techniques provide excellent anatomic visualization and functional information. They can be used to measure neural fiber track development and have a number of potential clinical uses including, but not limited, to diagnosis of brain trauma, cardiac abnormalities, congenital defects and the assessment of lung development.

There are, however, a number of challenges in the use of MRI for neonatal imaging. Patient access during scanning can be difficult as MR magnets are typically large and surround the patient. Safety concerns include forces on ferromagnetic objects, potential for rf heating and acoustic noise. Also, logistics may be difficult, as MR scanners tend to be in radiology departments, while neonate infants are typically in the NICU.

FIGS. 1a-1d depict an exemplary MRI and incubator system 100 in or for which the techniques for the MR imaging of neonates in accordance with the present disclosure may be implemented. The illustrated MRI system comprises an MM scanner 102. Since the components and operation of the MRI scanner are well-known in the art, only some basic components helpful in the understanding of the system 100 and its operation will be described herein.

The MM scanner 102 may comprise a cylindrical superconducting magnet 104, which generates a static magnetic field within a bore 105 of the superconducting magnet 104. The superconducting magnet 104 generates a substantially homogeneous magnetic field within the magnet bore 105. The superconducting magnet 104 may be enclosed in a magnet housing 106.

A set of cylindrical magnetic field gradient coils 112 may also be provided within the magnet bore 105. The gradient coils 112 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 114 is positioned within the gradient coils 112. The RF transmitter coil 114 emits RF energy in the form of a magnetic field for the purpose of exciting MR signals during image acquisition. The RF transmitter coil 114 can also receive MR response signals. The MR response signals are amplified, conditioned and digitized into raw data as is known by those of ordinary skill in the art.

The present disclosure provides an apparatus and a technique for safely and effectively transferring an infant from the primary care area, such as an incubator, to the MR magnet. In one particular embodiment, the present disclosure provides the means to transfer a neonate from the NICU to an MR magnet located either in a radiology department or in the NICU itself. The present disclosure accomplishes this by providing an MR-compatible transfer table assembly that can be easily attached to and removed from the infant's incubator without disturbing the infant. This assembly creates an MR compatible extension to the incubator that the baby can be moved into without being detached from patient monitoring or life support systems. Once stabilized in the assembly, the incubator, baby and transfer table assembly can then be moved as a unit to the magnet, where the transfer table assembly and baby are inserted into the magnet, without the need to insert the incubator into the magnet. In the present disclosure the incubator does not need to be fully MR compatible and can be constructed with some MR incompatible elements such as electrical motors.

Referring again to FIGS. 1a-1d, an incubator 130 containing a neonate 110 lying on an incubator bed 108 is shown. The incubator 130 has an optional top 132 that can be left in place or alternatively moved away from the neonate. The walls of the incubator may be clear and may provide one or more incubator access ports 134 to permit attending medical staff to reach into the incubator. The incubator may have a front panel 136 that can be removed or rotated out of the way to provide wider access to the neonate 110.

FIG. 1b shows the attachment of a transfer table assembly according to the present disclosure (shown later as element 200 of FIG. 2) to the incubator 130. This transfer table assembly according to the present disclosure may include of a transfer table 120, a transfer table base 122 and a transfer table cover 124. The transfer table 120 may be positioned at substantially the same level as the base of the incubator bed 108 and is designed to receive and support all or a portion of the incubator bed 108. The transfer table base 122 may serve to support the transfer table 120, and in one embodiment may be constructed with clear plastic. In one embodiment of the present disclosure, the transfer table cover 124 may also constructed of clear plastic. The transfer table cover may optionally be attached by hinges to the transfer table base 122 or, in another embodiment, may be inserted with locking pins or other affixation mechanisms. In another embodiment of the disclosure, the transfer table cover 124 can be made removable and not used if desired.

FIG. 1c shows the placement of the neonate 110 and incubator bed 108 on the transfer table 120. In one embodiment of the present disclosure, neonate 110 is prepared for MR scanning while in this location. Preparations may include but are not limited to patient safety checks, swaddling, attachment of additional monitoring equipment, placement of MR receive coils, and/or attachment of hearing protection to the neonate 110.

Figure 1D:
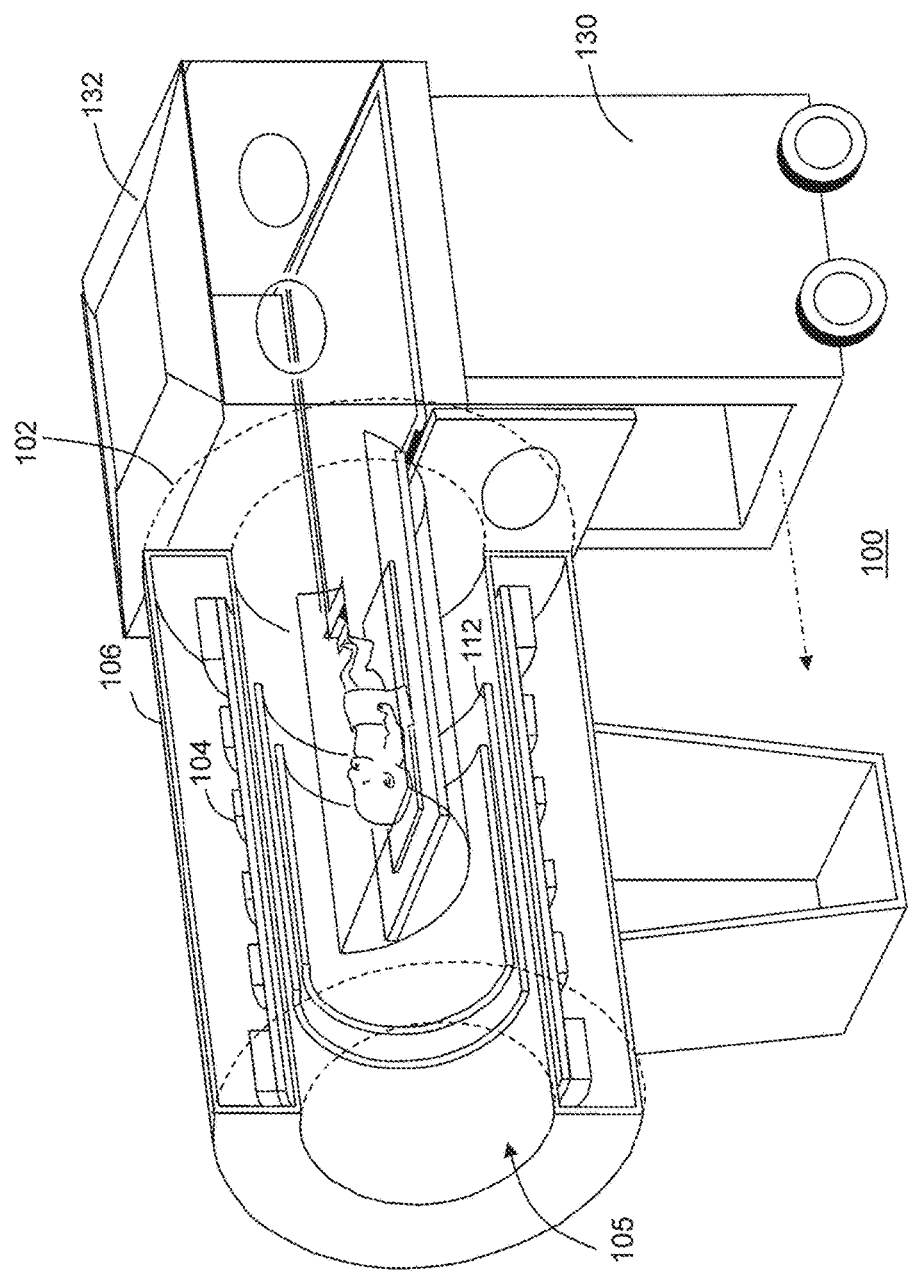
FIG. 1d is a perspective view showing the placement of the ensemble of incubator, transfer table assembly and neonate into an MR imaging system.

FIG. 1d shows the insertion of the transfer table assembly with the neonate into the MR imaging system 102. Note that during this insertion the neonate is not moved with respect to the incubator bed 108, the incubator 130, or the transfer table assembly.

Figure 2:
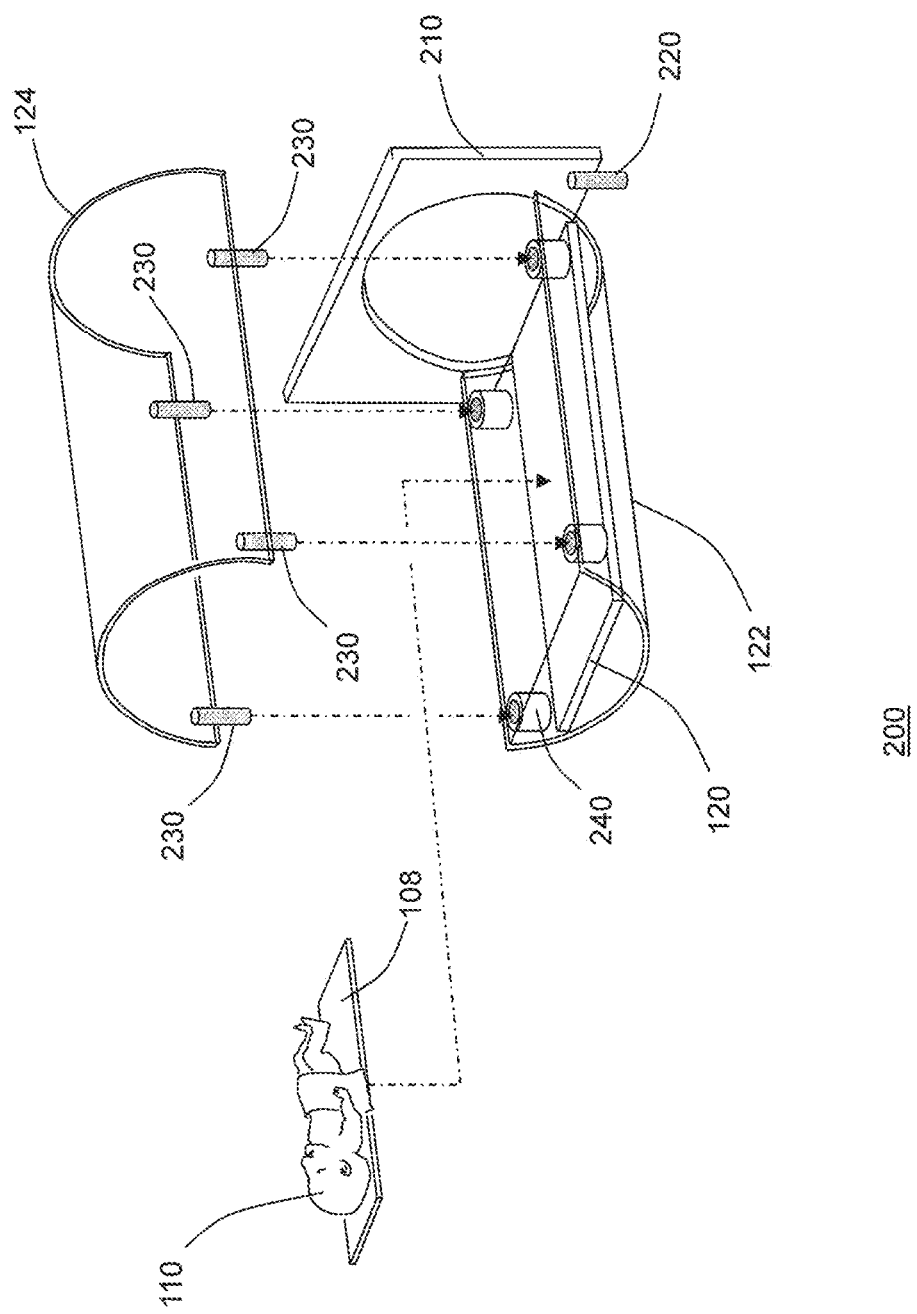
FIG. 2 is a partially exploded perspective view showing an embodiment of the MR-compatible transfer table assembly of the present disclosure.

FIG. 2 shows one embodiment of a transfer table assembly 200 in greater detail. The transfer table assembly 200 may include the transfer table 120, the transfer table base 122 and the transfer table cover 124. The transfer table base 122 and transfer table 120 may be attached to an end plate 210 which may provide additional structural support and serve to keep the incubator 130 enclosed when the incubator front panel 136 is not in position. End plate 210 may incorporate one or more assembly insertion pins 220 that are configured to align and attach the transfer table assembly 200 to the incubator 130. The pin assembly shown here is exemplary. It should be understood that the attachment of the transfer table assembly 200 to the incubator 130 can be accomplished by alternative means including, but not limited to, wing-nuts, slots, clamps and the like. Transfer table base 122, transfer table cover 124, and the end plate may be constructed of clear plastic material. The endplate may be formed from non-metallic material although small amounts of MR compatible metals such as aluminum, stainless steel, brass, etc. may be used. In one embodiment, the transfer table cover 124 may incorporate one or more cover locking pins 230 that may be designed for insertion into a like number of corresponding cover pin sockets 240. The cover locking mechanism shown here is exemplary. It should be understood that alternate mechanisms for attaching the transfer table cover 124 to the transfer table base 122, including, but not limited to hinges, slots, clamps and slides are covered by the spirit of the disclosure. If desired, neonate access ports similar to the incubator access ports 134 found in the incubator 130 can be incorporated into the transfer table cover 124. It should be obvious to one skilled in the art that the transfer table assembly may be constructed using MR compatible materials. It should also be obvious to one skilled in the art that the walls of the transfer table cover may be designed to attenuate the acoustic noise for the neonate 110.

Figure 2A:
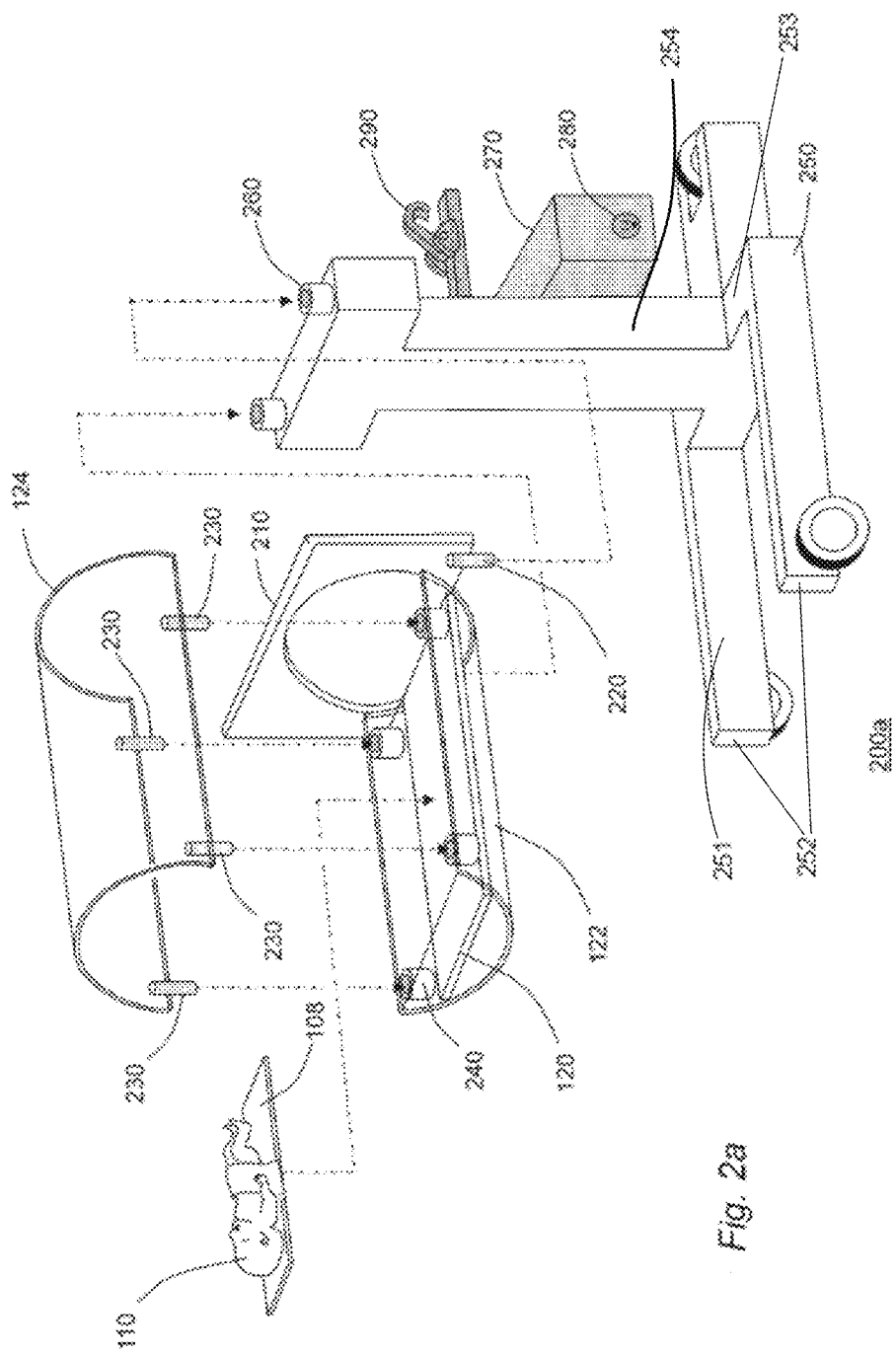
FIG. 2a is a partially exploded perspective view of an alternate embodiment of the MR-compatible transfer table assembly adapted to be secured to a cart.

FIG. 2a shows an alternate embodiment 200a of the transfer table assembly. In this embodiment, the assembly itself is substantially the same as disclosed in FIG. 2, but incorporates the ability to be attached to a transfer table cart 250. As shown in FIG. 2a, the transfer table cart 250 may include a wheeled, substantially wheel-level, horizontal support 251 structure with a leading end 252 and a trailing end 253, and having a vertical support 254 extending up from the trailing end 253 of the wheeled horizontal support structure 251. As shown in FIGS. 2 and 2a, the transfer table assembly 200 may include a supporting mechanism 210 such as an end plate 210. Supporting mechanism 210 may couple the transfer table base 122 to the transfer table cart 250. As shown in FIG. 2a, supporting mechanism 210 may couple the transfer table base 122 to the transfer table cart 250 in a cantilevered fashion. As shown when viewing FIGS. 2, 2a, and 3 together, supporting mechanism 210 may couple the transfer table base 122 to the transfer table cart 250 in a cantilevered fashion such that the transfer table base 122 is cantilevered from the transfer table cart 250 at substantially the same vertical level of the scanning bore of the MR scanner 102. Transfer table cart 250 may have one or more sockets 260 for receiving the assembly insertion pins 220. It should be understood that the attachment of the transfer table assembly 200a to the transfer table cart 250 can be accomplished by alternative means including, but not limited to, wing-nuts, slots, clamps and the like. Transfer table cart 250 may incorporate several features including a frame and wheel design that permits the transfer table cart 250 to dock to the MRI scanner 102. This allows the transfer table assembly to be inserted into the magnet while the transfer table cart 250 is supporting the weight of the transfer table assembly. In yet another embodiment of the disclosure, transfer table cart 250 may incorporate a docking mechanism 290 for attaching the transfer table cart 250 to the incubator 130. This provides for a way to affix the transfer table assembly 200 to the incubator 130 without requiring lifting of the transfer table assembly 200 and without requiring the incubator 130 to support a substantial portion of the weight of the transfer table assembly 200. In another embodiment of the transfer table cart 250, a power supply 270 is incorporated into the cart. The power supply 270 may incorporate a battery pack and inverter to provide AC power to the incubator 130 via an on-board electrical socket 280.

The present disclosure is particularly advantageous in that it may minimize the transfer time from the NICU to an MR imaging system 102 and may provide less stress on the infant. Another advantage of the present disclosure is that babies do not need to be fully detached from their home incubator which is shown as incubator 130 in FIGS. 1a-1d. Physiological monitoring leads, IV tubes, ventilator tubes and temperature sensors can be left in place throughout the imaging process. This further reduces preparation times and stress on the infant. An important aspect of the present disclosure is that the infant can be prepared for MR scanning while the incubator 130 and transfer table assembly are outside of the magnet. Once the baby is stabilized, the ensemble of baby, transfer table assembly and incubator can be inserted into the magnet to place the baby in the imaging region of the MM scanner. This approach ensures that the local environment of the baby is not altered as it is brought into the center of the imaging system. Furthermore, because a transport incubator is not required, and since the home incubator need not be fully MR-compatible, the MR magnet can be small and lightweight. This makes it more easily installed within the confines of the NICU, and provides improved access to MR for premature babies. In addition, the present disclosure permits MR scanning to be performed with fewer support personnel, and/or places support personnel closer to the other babies present in the NICU. With the present disclosure MR imaging may be made available to all babies in a NICU (typically between 10 and 60) using a single MR magnet and a single transfer table assembly that may be installed as needed into each and every compatible incubator in the NICU.

In particular, the present disclosure relates to a transfer table assembly for preparing an infant, including neonates, prior to transfer into the magnet. In the present disclosure the transfer table assembly is an extension that may be selectively physically attached to an incubator 130 that is actively supporting an infant. In a typical embodiment, one wall of the incubator may be removed or repositioned out of the way. The transfer table assembly may then attached to the incubator 130. The assembly may be designed to expand the interior volume of the incubator, but may have an external profile that permits the assembly to be inserted into an MR imaging system. The assembly may incorporate a platform that permits the neonate to be moved from its position in the incubator into the table assembly. The platform may be constructed to permit the infant's bed, or a portion of the bed, to be rolled from the incubator into the table assembly without disturbing or touching the infant.

Once the infant is in the MR-compatible transfer table assembly 200, the infant may be prepared for MR scanning. As will be recognized by those skilled in the art of MR scanning, MR scanning frequently requires that several steps be performed before a patient can be inserted into an imaging magnet. These steps may include: a) immobilization of the patient (in the case of neonatal imaging, swaddling is frequently sufficient), b) the optional insertion of IV tubes for contrast injections, c) the attachment of MR imaging coils, d) a safety check to verify that no ferromagnetic objects are present, e) placement of hearing protection, and f) verification of patient stability and comfort. All of these steps may need to be performed while the patient is near the magnet, and may require access to the patient which is not possible with most incubator designs.

Another aspect of the transfer table assembly of the present disclosure is that it may provide full environmental control for the neonate. Many neonates are too young to be able to fully control their internal temperature, and it is well known to those skilled in the art that small neonates must be kept warm. In the present disclosure, this can be done with warm air and/or a radiant heater located in the infants incubator 130. In one embodiment of the disclosure, a thermocouple or similar temperature sensor modified for use in the MR environment with non-ferromagnetic parts and appropriate rf filtering may be used to provide feedback to the incubator's temperature control system to provide suitable temperature control. In another embodiment of the disclosure, baffles may be provided to route heated air from the incubator 130 into and through the transfer table assembly 200.

The transfer table assembly of the present disclosure may be attached to the infant's incubator 130. One major function of the assembly may be to act as a buffer element to prevent non MR-compatible objects from entering into the magnet while the baby is inside the assembly.

Figure 3:
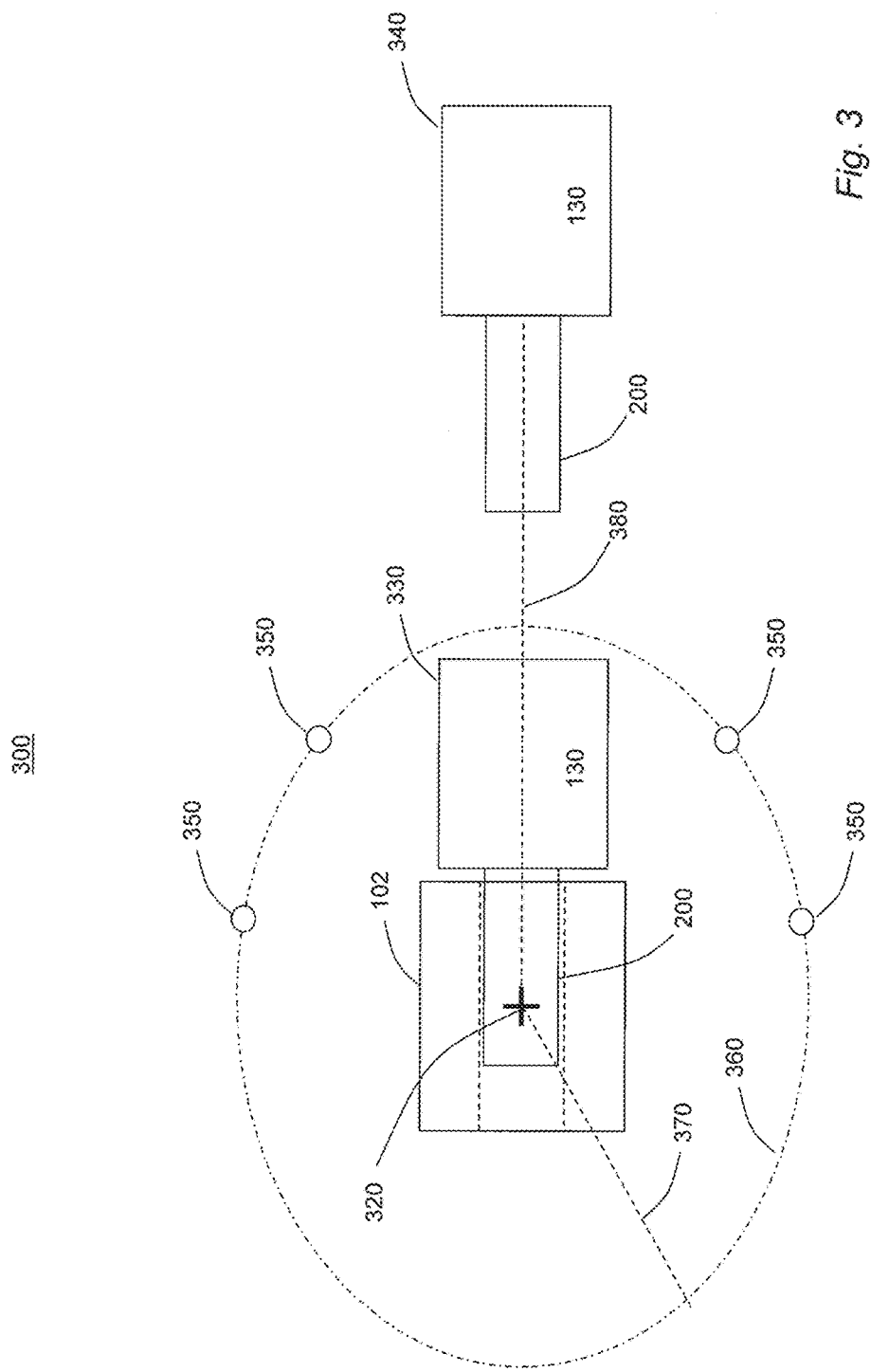
FIG. 3 shows a top-plan view of an MR magnet and incubator with barrier poles to limit access of the incubator to the magnet.

As shown in FIG. 3, the safety barrier provided by the transfer table assembly 200 may be augmented with in-room barriers such as poles 350 in the floor spaced to prevent incubators or other devices from getting within a predetermined fringe magnetic field strength 360 (typically chosen to be 5 Gauss) at a selected distance 370 of the magnet. With such an approach the incubator 130 may be placed into a pre-dock position 340 where the transfer table assembly 220 may be attached and the neonate 110 may be moved and prepared for MR scanning. The ensemble of the transfer table assembly 200, neonate 110 and incubator 130 may then be moved towards MR scanner 102 along docking route 380. When the ensemble is in a docked location 330, the neonate 110 may be positioned at the isocenter 320 of the MR scanner 102.

Figure 4:
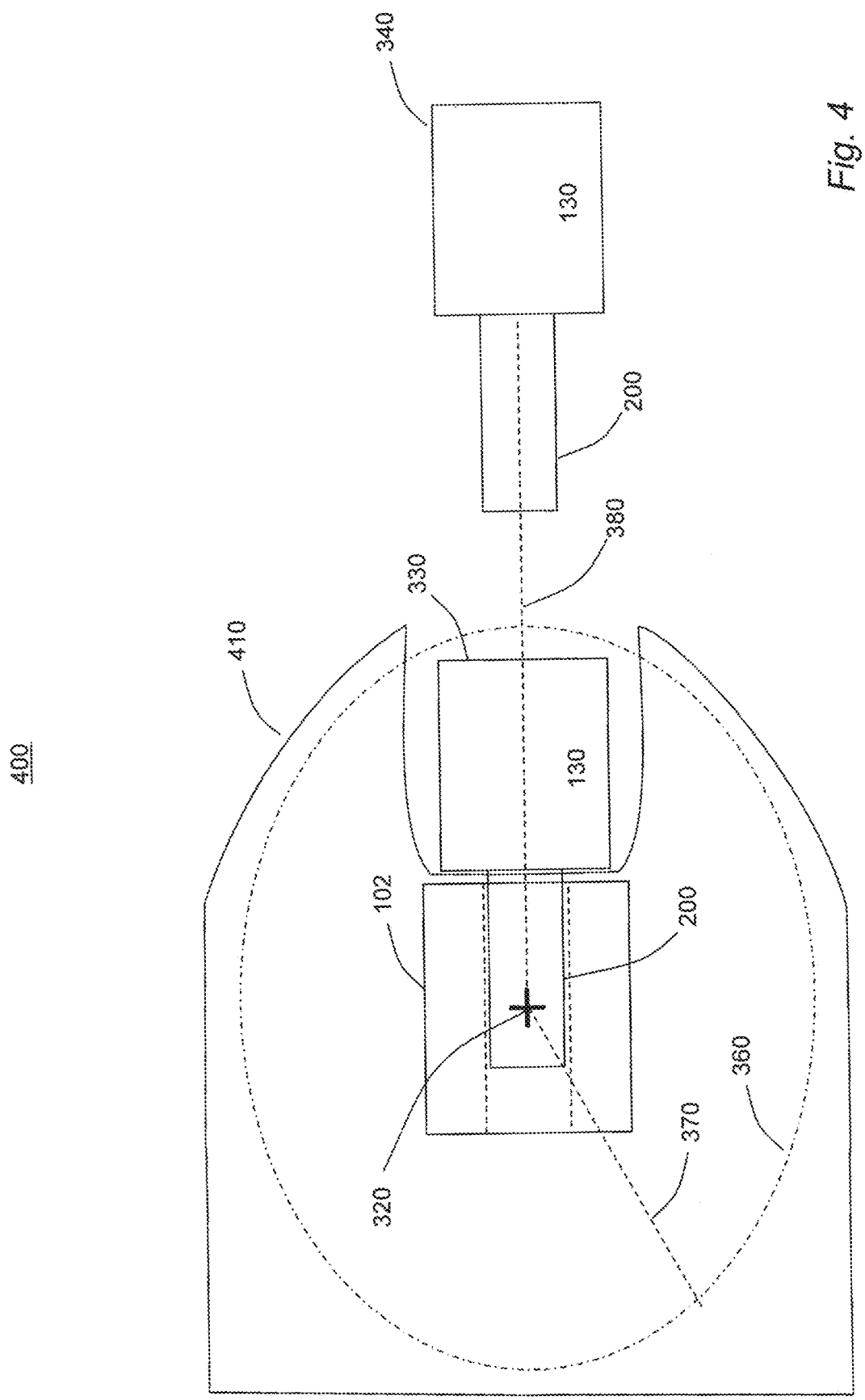
FIG. 4 shows a top-plan view of an MR magnet and incubator with an elevated floor barrier to limit access of the incubator to the magnet.

Alternatively, the barrier may be augmented with a step design as shown in FIG. 4 in which the floor that accommodates the NICU incubator may be lower than a raised floor 410 surrounding the magnet. The step created by the two levels of the floor acts to align the incubator to the magnet as the transfer table assembly is inserted into the magnet. In an alternative embodiment of the disclosure, alignment mechanisms may be placed on the floor or at the base of the magnet to ensure proper alignment of the incubator during insertion.

The present disclosure has the advantage of working with incubators and isolettes that do not require modification to be made MR compatible. According to the present disclosure, the infant may, in one embodiment, still be tethered to the incubator by life support and monitoring methods, for example IV lines and EKG leads. Alternatively, the transfer table assembly 200 itself may be equipped with some or all of the aforementioned life support and monitoring methods.

The transfer table assembly may in one embodiment, as shown in FIG. 1b and FIG. 1c, be open like an isolette. In one embodiment, the open isolette may be configured with radiant heating. In another embodiment, the transfer table may be enclosed like an incubator with the addition of a cover. In one embodiment, the enclosed transfer table assembly may be configured to provide warm circulating air.

In one embodiment of the disclosure, the incubator may be adapted to dock to the MR scanner. This may be accomplished for instance by a mechanical latch which rigidly engages and may require a physical action to unlock, or it could be a simple "tongue and groove" arrangement in which the incubator can be brought close to the MR scanner with a selected alignment. In such an arrangement, it may be desirable to engage the wheel brakes on the incubator during docking to prevent the incubator from moving unexpectedly.

As mentioned, in one embodiment, the transfer table assembly 200 may be equipped to include all necessary life support and monitoring equipment. Such equipment includes, but is not limited to, EKG monitoring, IV tubes, oxygen monitors, ventilators, breathing gases, and bilirubin treatment. If needed, the transfer table assembly 200 can be powered by attachment to the incubator, an external supply or an on-board MR-compatible battery.

In one embodiment of the disclosure, the transfer table assembly 200 may comprise physical barriers to prevent extraneous objects being sucked into the infant when the infant is inside the magnet. In one embodiment, the barrier may comprise a full enclosure made of clear engineering plastic that is resistant to impact damage. This provides full visual access of the baby but provides a barrier to the entry of other objects into the magnet.

In one embodiment, a Faraday cage may be built into the transfer table assembly 200 to prevent RF interference from degrading the MR image. This would be particularly advantageous if the MR system is not placed in an RF screen room. Should a Faraday cage be incorporated into the transfer table assembly, an internal rf tight panel or door may need to be added between the incubator and the transfer table assembly. It may also be desirable to provide penetration filters for monitoring leads to minimize rf interference during MR imaging.

In an even further embodiment, the transfer table assembly may incorporate a scale for weighing the infants.

While the foregoing description includes many details and specificities, it is to be understood that these have been included for purposes of explanation only, and are not to be interpreted as limitations of the present disclosure. It will be apparent to those skilled in the art that other modifications to the embodiments described above can be made without departing from the spirit and scope of the disclosure. Accordingly, such modifications are considered within the scope of the disclosure as intended to be encompassed by the following claims and their legal equivalents.

What is claimed is:

1. A transfer table assembly and cart apparatus for use in scanning neonatal infants with an MR scanner, the transfer table assembly and cart apparatus comprising:
 a transfer table assembly comprising an MR-compatible transfer table base and a supporting mechanism, the transfer table base being sized and shaped to receive a neonatal infant thereon;
 wherein the supporting mechanism couples the transfer table base to a movable transfer table cart in a cantilevered fashion such that the transfer table base is cantilevered from the transfer table cart at substantially the same vertical level of a scanning bore of an MR scanner;
 wherein the transfer table cart includes a frame designed to dock with the MR scanner; and
 wherein the cantilevered transfer table base is sized to be received in the scanning bore of the MR scanner and is positioned coaxially with the scanning bore of the MR scanner when docked with the MR scanner.

2. The transfer table assembly and cart apparatus of claim 1, wherein the transfer table base is configured to receive an incubator bed thereon.

3. The transfer table assembly and cart apparatus of claim 1, wherein the frame of the transfer table cart is designed to dock with the MR scanner in a tongue-and-groove arrangement.

4. The transfer table assembly and cart apparatus of claim 1, wherein the supporting mechanism releasably couples the transfer table base to the transfer table cart.

5. The transfer table assembly and cart apparatus of claim 1, further comprising a transfer table cover attached to the transfer table base, the transfer table cover and the transfer table base defining a space configured to house a neonatal infant during an MR scan.

6. The transfer table assembly and cart apparatus of claim 1, wherein the supporting mechanism comprises an end plate extending substantially perpendicularly from the transfer table base and providing structural support to the transfer table base when the transfer table base is attached to the transfer table cart, the end plate abutting a portion of the transfer table cart to provide structural support to the transfer table assembly.

7. The transfer table assembly and cart apparatus of claim 6, wherein the end plate further comprises one or more pins aligning and releasably attaching the transfer table assembly to the transfer table cart.

8. The transfer table assembly and cart apparatus of claim 1, wherein the transfer table assembly is equipped with life support and monitoring equipment.

9. The transfer table assembly and cart apparatus of claim 6, wherein the transfer table assembly is configured as an open isolette.

10. A system for providing MR scans to neonatal infants, comprising:
 an MR scanner located within the confines of a neonatal intensive care unit; and
 a transfer table assembly and cart apparatus comprising:
  a transfer table assembly comprising an MR-compatible transfer table base and a supporting mechanism, the transfer table base sized and shaped to receive a neonatal infant thereon;
  wherein the supporting mechanism couples the transfer table base to a movable transfer table cart in a cantilevered fashion such that the transfer table base is cantilevered from the transfer table cart at substantially the same vertical level of a scanning bore of the MR scanner;
  wherein the transfer table cart includes a frame designed to dock with the MR scanner; and
  wherein the cantilevered transfer table base is sized to be received in the scanning bore of the MR scanner and is positioned coaxially with the scanning bore of the MR scanner when docked with the MR scanner.

11. The system of claim 10, further comprising one or more barriers positioned to prevent a non-MR-compatible incubator from travelling to a point closer to the MR scanner where the magnetic field strength is greater than or equal to about 5 Gauss.

12. The system of claim 10, wherein the transfer table cart includes a frame designed to dock with the MR scanner in a tongue-and-groove arrangement.

13. The system of claim 10, wherein the supporting mechanism releasably couples the transfer table base to the transfer table cart.

14. The system of claim 10, wherein the transfer table assembly further comprises a transfer table cover attached to the transfer table base, the transfer table cover and the transfer table base defining a space configured to house a neonatal infant during an MR scan.

15. The system of claim 10, wherein the supporting mechanism comprises an end plate extending substantially perpendicularly from the transfer table base when the transfer table base is attached to the transfer table cart, the end plate abutting a portion of the transfer table cart to provide structural support to the transfer table assembly.

16. The system of claim 15, wherein the end plate further comprises one or more pins aligning and releasably attaching the transfer table assembly to the transfer table cart.

17. The system of claim 10, wherein the transfer table assembly is equipped with life support and monitoring equipment.

18. The system of claim 10, wherein the transfer table assembly is configured as an open isolette.

19. A method of providing a neonatal infant with an MR imaging scan, the method comprising the steps of:
 a) providing a transfer table assembly configured to support a neonatal infant coupled to a transfer table cart in a cantilevered fashion such that the transfer table assembly is cantilevered from the transfer table cart substantially at the same vertical level of a scanning bore of an MR scanner, the MR scanner being located in a neonatal intensive care unit, the transfer table assembly further being substantially MR compatible, the transfer table assembly including a transfer table base dimensionally constructed to be inserted into the scanning bore of the MR scanner, the transfer table cart including a frame designed to dock with the MR scanner; the cantilevered transfer table assembly being positioned coaxially with the scanning bore of the MR scanner when the frame of the transfer table cart is docked with the MR scanner;
 b) transferring the neonatal infant onto the transfer table assembly;

c) preparing the neonatal infant for MR scanning;

d) positioning the neonatal infant within the scanning bore of said MR scanner by engaging the transfer table assembly and transfer table cart combination with the MR scanner, wherein said transfer table assembly is inserted within the scanning bore of the MR scanner; and e) activating the MR scanner to obtain MR imaging of the neonatal infant.

20. The method of claim 19 wherein the transfer table base is configured to removably couple with an incubator bed.

21. A transfer table assembly and cart apparatus for use in scanning neonatal infants within an MR scanner, the transfer table assembly and cart apparatus comprising:
   a transfer table cart having a wheeled, substantially wheel-level, horizontal support structure with a leading end and a trailing end, and having a vertical support extending up from the trailing end of the wheeled horizontal support structure;
   an MR-compatible transfer table assembly coupled to the vertical support of the wheeled horizontal support structure in a cantilevered fashion substantially at the same vertical level of a scanning bore of an MR scanner, and extending horizontally from the vertical support in a direction towards the leading end of the wheeled horizontal support structure; and
   an infant bed contained within the transfer table assembly.

22. The transfer table assembly and cart apparatus of claim 21, wherein the transfer table assembly has a cross-sectional width and height sized to be received within a scanning bore of an MR scanner.

23. The transfer table assembly and cart apparatus of claim 21, wherein the transfer table cart includes an integrated power supply.

24. The transfer table assembly and cart apparatus of claim 23, wherein the transfer table assembly includes a cover for enclosing the infant bed therein forming an infant bed enclosure, and further includes a heater powered by the integrated power supply for heating the infant bed enclosure.

25. The transfer table assembly and cart apparatus of claim 21, wherein the transfer table assembly includes a cover for enclosing the infant bed therein, forming an infant bed enclosure.

26. The transfer table assembly and cart apparatus of claim 25, wherein the cover is at least partially transparent so that the infant bed may be viewed from outside when the cover is attached.

27. The transfer table assembly and cart apparatus of claim 25, wherein the cover includes one or more access ports allowing a care-giver's hands access within the infant bed enclosure.

28. The transfer table assembly and cart apparatus of claim 21, wherein the infant bed is horizontally moveable at least partially into and out of an end of the transfer table assembly.

* * * * *